United States Patent [19]

Wiedemann et al.

[11] 4,143,149
[45] Mar. 6, 1979

[54] INDAZOLYL-(4)-OXYPROPANOLAMINE COMPOUNDS AND THERAPEUTIC COMPOSITIONS

[75] Inventors: Fritz Wiedemann, Weinheim-Lützelsachsen; Wolfgang Kampe, Heddesheim; Max Thiel, Mannheim; Wolfgang Bartsch, Viernheim; Egon Roesch, Mannheim, all of Fed. Rep. of Germany

[73] Assignee: Boehringer Mannheim GmbH, Mannheim-Waldhof, Fed. Rep. of Germany

[21] Appl. No.: 790,648

[22] Filed: Apr. 25, 1977

[30] Foreign Application Priority Data

Apr. 30, 1976 [DE] Fed. Rep. of Germany ....... 2619164

[51] Int. Cl.² .................. A61K 31/415; C07D 231/56
[52] U.S. Cl. ................................ 424/273 P; 548/371; 548/372; 260/307 A
[58] Field of Search ............................. 548/371, 372; 424/273 P

[56] References Cited

U.S. PATENT DOCUMENTS 3,843,678  10/1974  DiBella .............................. 548/371
3,920,691  11/1975  Wasson et al. ..................... 424/273 P
3,966,761  6/1976   Podesva et al. .................... 424/273 P

FOREIGN PATENT DOCUMENTS 7631M  1/1970 France.

Primary Examiner—Natalie Trousof
Assistant Examiner—Natalia Harkaway
Attorney, Agent, or Firm—Sprung, Felfe, Horn, Lynch & Kramer

[57] ABSTRACT

New indazolyl-(4)-oxypropanolamine compounds of the formula

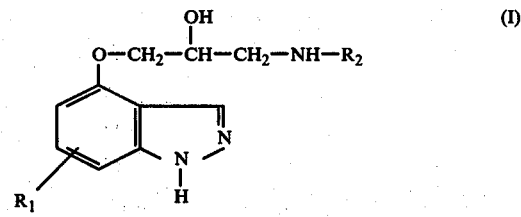

wherein
  $R_1$ is hydrogen or lower alkyl; and
  $R_2$ is straight-chain or branched lower alkyl which can be substituted by lower alkylthio;

and the pharmacologically compatible salts thereof; are outstandingly effective adrenergic β-receptor inhibitors and useful in the treatment or prevention of a recurrence of cardiac and circulatory diseases.

16 Claims, No Drawings

INDAZOLYL-(4)-OXYPROPANOLAMINE COMPOUNDS AND THERAPEUTIC COMPOSITIONS

The present invention is concerned with new indazolyl-(4)-oxypropanolamine compounds and with therapeutic compositions and methods useful in the treatment of cardiac and circulatory diseases, utilizing such compounds.

The new indazolyl-(4)-oxypropanolamines according to the present invention are compounds of the formula:

(I)

wherein
 $R_1$ is hydrogen or lower alkyl; and
 $R_2$ is straight-chain or branched lower alkyl which can be substituted by lower alkylthio; and the pharmacologically compatible salts thereof.

The new compounds (I), as well as the pharmacologically-compatible salts thereof, bring about an inhibition of adrenergic β-receptors and can, therefore, be used for the treatment or prevention of a recurrence of cardiac and circulatory diseases.

The new compounds (I) according to the present invention can be prepared, for example, by one of the following methods:

a. reaction of a compound of the general formula:

$$O-CH_2-X-CH_2-Y \quad (II)$$

with a compound of the general formula:

$$Z - R_2 \quad (III)$$

wherein $R_1$ and $R_2$ have the same meanings as above, R' is a hydrogen atom or an acyl radical, one of the symbols Y and Z represents an amino group and the other represents a reactive residue and X is a =C=O or =CH—A group, A being a hydroxyl group or, together with Y, representing an oxygen atom; or b. reaction of a 4-hydroxyindazole of the general formula:

(IV), wherein $R_1$ and R' have the same meanings as above, with a compound of the general formula:

$$Y'-CH_2-X-CH_2-NH-R_2 \quad (V)$$

wherein X and $R_2$ have the same meanings as above and Y' is a reactive residue; or c. saponification of a compound of the general formula:

(VI)

wherein R', $R_1$ and $R_2$ have the same meanings as above and A is a =C=O or =CR"(R''') group, R" and R''', which may be the same or different, being hydrogen atoms or lower alkyl or aryl radicals; or of a compound of the general formula:

(VII)

wherein R', $R_1$ and $R_2$ have the same meanings as above; after the reaction a protective group R' possibly present is then split off and, when X is a =C=O group, this is reduced; and the compound obtained of general formula (I) is, if desired, converted into a pharmacologically compatible salt.

The lower alkyl radical substituents $R_1$ can contain up to 4 carbon atoms, the methyl radical being preferred.

The lower alkyl radical substituents $R_2$ can contain up to 5 carbon atoms, the isopropyl and tert.-butyl radicals being preferred.

The lower alkylthio radical can contain up to 3 carbon atoms, the methylthio radical being preferred.

The protective acyl radical R' is to be understood to be a radical containing up to 7 carbon atoms, the acetyl and benzoyl radicals being preferred.

Reactive radicals Y, Y' and Z in the compounds of general formulae (II), (III) and (V) are preferably acid residues, for example of hydrohalic acids or sulphonic acids.

Compounds of general formula (II) are also new. They can be obtained, for example, from 4-hydroxyindazoles by reaction with reactive compounds of the general formula:

$$Y'-CH_2-X-CH_2-Y \quad (VIII)$$

wherein Y, Y' and X have the same meanings as above.

The processes according to the present invention are preferably carried out in an organic solvent which is inert under the reaction conditions, for example toluene, dioxan, ethylene glycol dimethyl ether, ethanol, n-butanol or dimethyl formamide, possibly in the presence of an acid-binding agent. However, the reaction can also be brought about, after mixing the reaction components, by leaving the reaction mixture to stand at ambient temperature or by heating it.

The reaction of compounds of general formula (IV) with compounds of general formula (V) according to process (b) is preferably carried out with the exclusion of oxygen and in the presence of an acid acceptor. However, an alkali metal salt of the hydroxy compound of general formula (IV) can also be used.

The compounds of general formulae (VI) and (VII) can be prepared in known manner. Thus, for example, compounds of general formula (VI) can be obtained by the reaction of 4-hydroxyindazoles of general formula (IV) with reactive esters of 5-hydroxymethyl-oxazolidines which are optionally substituted in the 2-position.

For the preparation of these esters, for example derivatives of 2,3-epoxypropanol, in which the hydroxyl group is etherified or esterified with a protective group, are reacted with amines of the general formula $H_2NR_2$, in which $R_2$ has the same meaning as above, the aminoalcohols thereby obtained are converted, by reaction with a reagent providing a carbonyl group, such as phosgene or carbonyl-bis-imidazole, into the oxazolidin-2-ones or with aldehydes or ketones into the oxazolidines, whereupon the protective group is split off and the 5-hydroxymethyl-oxazolidines thereby formed are esterified with a strong acid. The preferred protective group is the benzyl radical and the preferred strong acids are methane-sulphonic acid and p-toluene-sulphonic acid.

The compounds of general formula (VII) can be obtained from the allyl ethers of compounds of general formula (IV), via the bromine addition products, by reaction with appropriate primary amines.

The saponification of the compounds of general formulae (VI) and (VII) generally takes place in a water-containing medium in the presence of acids or bases.

If R' in general formulae (II), (IV), (VI) or (VII) represents an acyl radical, this can be split off under mild conditions by aminolysis or hydrolysis.

If it is necessary to reduce a =C=O group, this can be carried out, for example, by means of sodium borohydride or by catalytic hydrogenation in the presence of noble metal catalysts.

For the conversion of compounds of general formula (I) into their pharmacologically compatible salts, these are reacted, preferably in an organic solvent, with an equivalent amount of an inorganic or organic acid, for example hydrochloric acid, hydrobromic acid, phosphoric acid, sulphuric acid, acetic acid, citric acid, maleic acid or benzoic acid.

For the preparation of pharmaceutical compositions, the compounds (I) are mixed in known manner with appropriate solid or liquid pharmaceutical diluents or carriers and optionally with aroma, flavoring and coloring materials and formed, for example, into tablets or dragees or, with the addition of appropriate adjuvants, suspended or dissolved in water or in an oil, for example olive oil.

The compounds (I) according to the present invention and the salts thereof can be administered enterally or parenterally in liquid or solid form. As injection medium, it is preferable to use water which contains the additives usual in the case of injection solutions, such as stabilising agents, solubilising agents or buffers. Additives of this type include, for example, tartrate and citrate buffers, ethanol, complex-forming agents (such as ethylene-diamine-tetraacetic acid and the non-toxic salts thereof), and high molecular weight polymers (such as liquid polyethylene oxide) for viscosity regulation. Solid carrier materials include, for example, starch, lactose, mannitol, methyl cellulose, talc, highly-dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The following Examples are given for the purpose of illustrating the present invention:

EXAMPLE 1

1-[Indazolyl-(4)-oxy]-3-isopropylaminopropan-2-ol 12.5 g. 1-Acetyl-4-(2,3-epoxypropoxy)-indazole are heated under reflux for 3 hours in 50 ml. isopropylamine. The reaction mixture is then evaporated to dryness, the residue is triturated with diethyl ether and the product obtained is recrystallized from ethyl acetate. There are obtained 8.0 g. (60% of theory) 1-[indazolyl-(4)-oxy]-3-isopropylaminopropan-2-ol in the form of colorless crystals; m.p. 166°–167° C.

The 1-acetyl-4-(2,3-epoxypropoxy)-indazole used as starting material is prepared in several stages as follows:

a. (3-Amino-2-methylphenyl)-benzyl ether

By the reduction of (2-methyl-3-nitrophenyl)-benzyl ether with hydrazine hydrate and Raney nickel in methanol, there is obtained the crude product in the form of a green oil.

b. (3-Acetamino-2-methylphenyl)-benzyl ether

Acetylation of the product described in (a) with acetic anhydride in toluene gives the desired product in the form of colorless crystals; m.p. 142°–143° C. (after recrystallization from toluene).

c. 1-Acetyl-4-benzyloxy-indazole

A mixture of 64 g. (3-acetamido-2-methylphenyl)-benzyl ether, 25 g. sodium acetate, 69 ml. acetic anhydride, 50 ml. isoamyl nitrite and 2 liters toluene is stirred for 15–20 hours at 80°–90° C. After cooling the reaction mixture to 10° C., the salts are filtered off with suction and the filtrate is evaporated to dryness in a vacuum. By trituration of the residue with 300 ml. methanol, there are obtained 47.5 g. 1-acetyl-4-benzyloxy-indazole in the form of almost colorless crystals; m.p. 97° C.

d. 1-Acetyl-4-hydroxy-indazole

By the hydrogenolysis of the 4-benzyloxy compound obtained in (c) in the presence of palladium-charcoal (10%) in methanol at atmospheric pressure, there is obtained 1-acetyl-4-hydroxy-indazole in the form of beige crystals; m.p. 140°–142° C. (after recrystallization from water).

e. 1-Acetyl-4-(2,3-epoxypropoxy)-indazole

To 17 g. 1-acetyl-4-hydroxy-indazole, dissolved in 200 ml. anhydrous dimethyl sulphoxide, there are added, while stirring, 5 g. of a sodium hydride suspension (50–60% in paraffin) and, after termination of the evolution of hydrogen, 30 g. p-toluene-sulphonic acid 2,3-epoxypropyl ester are added thereto in 10 g. portions. The reaction mixture is then heated to 60° C. for 2 hours, poured into 2 liters water, acidified with acetic acid and extracted with methylene chloride. The extract is washed with water, dried with anhydrous sodium sulphate, treated with fullers' earth and then evaporated to dryness in a vacuum. The residue is triturated at −40° C. with 100–200 ml. methanol, filtered with suction and thereafter washed with methanol. There are obtained 12.5 g. 1-acetyl-4-(2,3-epoxypropoxy)-indazole in the form of colorless crystals; m.p. 83° C.

EXAMPLE 2

1-[Indazolyl-(4)-oxy]-3-tert.-butylaminopropan-2-ol 12.4 g. 1-Acetyl-4-(2,3-epoxypropoxy)-indazole and 50 ml. tert.-butylamine are boiled under reflux for 15 hours. The reaction mixture is evaporated to dryness and the residue is triturated with diethyl ether and then recrystallized from ethyl acetate. There are obtained 6.0 g. (42.6% of theory) 1-[indazolyl-(4)-oxy]-3-tert.-butylaminopropan-2-ol in the form of colorless crystals; m.p. 193°–194° C.

EXAMPLE 3

1-[Indazolyl-(4)-oxy]-3-[1-methylthiopropyl-(2)-amino]-propan-2-ol 3.5 g. 4-(2,3-Epoxypropoxy)-indazole are stirred in an atmosphere of nitrogen with 15 ml. methylthioisopropylamine for 7 hours at 60° C. The reaction mixture is evaporated to dryness in a vacuum and the residue is recrystallized from ethyl acetate. There is obtained 0.5 g. 1-[indazolyl-(4)-oxy]-3-[1-methylthiopropyl-(2)-amino]-propan-2-ol in the form of colorless crystals; m.p. 96°–98° C.

The 4-(2,3-epoxypropoxy)-indazole used as starting material is prepared as follows:

The 1-acetyl compound described in Example 1 is stirred in a mixture of methylene chloride and liquid ammonia (cooling with solid carbon dioxide) for 4 hours. Upon evaporating in a vacuum, there is obtained a brownish oil which is sufficiently pure for the reaction with amines. By stirring with water, there is obtained a beige product; m.p. about 60° C. (after melting, it solidifies again and then has a second melting point at > 260° C.).

EXAMPLE 4

1-[6-Methyl-indazolyl-(4)-oxy]-3-isopropylaminopropan-2-ol 5.0 g. 1-Acetyl-4-(2,3-epoxypropoxy)-6-methylindazole are heated under reflux for 6 hours with 25 ml. isopropylamine. The reaction mixture is evaporated to dryness and the residue is triturated with diethyl ether and then recrystallized from ethyl acetate, with the use of active charcoal and fullers' earth. There are obtained 2.8 g. (52.3% of theory) 1-[6-methyl-indazolyl-(4)-oxy]-3-isopropylaminopropan-2-ol in the form of colorless crystals; m.p. 157°–158° C.

The acetic acid salt of the compound is obtained by adding 1 ml. acetic acid to the filtrate obtained by the crystallization, evaporating to dryness, taking up the residue in a little methanol, mixing the solution with diethyl ether until a slight turbidity is obtained and, after triturating in the cold, leaving to crystallize. After recrystallization from ethyl acetate, the salt is obtained in the form of colorless crystals; m.p. 141°–142° C.

The 1-acetyl-4-(2,3-epoxypropoxy)-6-methylindazole used as starting material is obtained in several stages as follows:

a. (2,5-Dimethyl-3-nitrophenyl)-benzyl ether

A mixture of 433 g. 2,5-dimethyl-3-nitrophenol, 360 g. potassium carbonate, 326 ml. benzyl chloride and 2 liters dimethyl formamide is stirred overnight at 50° C. The reaction mixture is then filtered with suction and the filtrate is evaporated to dryness in a vacuum. The residue is poured on to 4 liters ice-water and, after suction filtration and drying in the air, there are obtained 668 g. (2,5-dimethyl-3-nitrophenyl)-benzyl ether in the form of yellowish crystals; m.p. 66°–68° C.

b. (3-Amino-2,5-dimethylphenyl)-benzyl ether

The nitro compound obtained in (a) above is reduced with hydrazine hydrate and Raney nickel in methanol to give, in good yield, crude (3-amino-2,5-dimethylphenyl)-benzyl ether in the form of a brown oil.

c. (3-Acetamino-2,5-dimethylphenyl)-benzyl ether

Acetylation of the amino compound obtained in (b) above with acetic anhydride in toluene gives (3-acetamino-2,5-dimethylphenyl)-benzyl ether in the form of colorless crystals; m.p. 169°–171° C. (after recrystallization from toluene).

d. 1-Acetyl-4-benzyloxy-6-methylindazole

A mixture of 149 g. (3-acetamino-2,5-dimethylphenyl)-benzyl ether, 50 g. sodium acetate, 138 ml. acetic anhydride, 50 ml. isoamyl nitrite and 3 liters toluene is stirred for 15–20 hours at 80°–90° C. After cooling, the reaction mixture is filtered with suction and the filtrate is evaporated to dryness in a vacuum. The residue is taken up in about 300 ml. methanol, whereupon the product crystallizes in the cold. There are obtained 103 g. 1-acetyl-4-benzyloxy-6-methylindazole in the form of yellowish crystals; m.p. 91°–93° C.

e. 1-Acetyl-4-hydroxy-6-methylindazole

The benzyl compound obtained according to (d) above is hydrogenated in the presence of palladium-charcoal (10%) in methanol at atmospheric pressure. 1-Acetyl-4-hydroxy-6-methylindazole is obtained in the form of pale yellowish crystals; m.p. 191°–192° C. (after recrystallization from methanol).

f. 1-Acetyl-4-(2,3-epoxypropoxy)-6-methylindazole 19 g. of the hydroxy compound obtained according to (e) above, 16.4 g. epibromohydrin and 16.6 g. potassium carbonate are stirred at 60° C. for 20 hours in 100 ml. dimethyl formamide. The reaction mixture is then poured on to water and extracted with methylene chloride. The extract is dried with anhydrous sodium sulphate, treated with fullers' earth and evaporated to dryness in a vacuum. After taking up the residue in 100 ml. methanol, the product crystallizes. There are obtained 11.0 g. 1-acetyl-4-(2,3-epoxypropoxy)-6-methylindazole in the form of colorless crystals; m.p. 105°–107° C.

EXAMPLE 5

1-[6-Methyl-indazolyl-(4)-oxy]-3-tert.-butylaminopropan-2-ol 5.0 g. 1-Acetyl-4-(2,3-epoxypropoxy)-6-methylindazole and 25 ml. tert.-butylamine are boiled under reflux for 9 hours. The reaction mixture is then evaporated to dryness, the residue is triturated with diethyl ether and the product is recrystallized from ethyl acetate. There are obtained 1.2 g. (21.3% of theory) 1-[6-methylindazolyl-(4)-oxy]-3-tert.-butylaminopropan-2-ol in the form of colorless crystals; m.p. 174°–175° C.

The acetic acid salt of the compound is prepared in a manner analogous to that described in Example 4 and is obtained in the form of colorless crystals; m.p. 156°–157° C. (after recrystallization from ethyl acetate).

In an analogous manner, there is obtained:

a. by the reaction of 1-acetyl-4-(2,3-epoxypropoxy)-6-methyl-indazole with sec.-butylamine:
  1-[6-methyl-indazolyl-(4)-oxy]-3-sec.-butylamino-propan-2-ol;

b. by the reaction of 1-acetyl-4-(2,3-epoxypropoxy)-5-methyl-indazole with isopropylamine; m.p. 75°–76° C.
  1-[5-methyl-indazolyl-(4)-oxy]-3-isopropylaminopropan-2-ol; m.p. 123°–124° C.

The 1-acetyl-4-(2,3-epoxypropoxy)-5-methyl-indazole used as starting material is prepared by several stages analogously to the process used for the preparation of the corresponding 6-methyl-indazole compound (cf. the process stages described in Example 4(a)–(f).

c. by the reaction of 1-acetyl-4-(2,3-epoxypropoxy)-5-methyl-indazole with tert.-butylamine:
  1-[5-methyl-indazolyl-(4)-oxy]-3-tert.-butylamino-propan-2-ol; m.p. 124°–125° C.

d. by the reaction of 1-acetyl-4-(2,3-epoxypropoxy)-7-methyl-indazole with isopropylamine; m.p. 108°–109° C.
  1-[7-methyl-indazolyl-(4)-oxy]-3-isopropylamino-propan-2-ol; m.p. 135°–136° C.

The 1-acetyl-4-(2,3-epoxypropoxy)-7-methyl-indazole used as starting material is prepared by several stages in a manner analogous to that used for the preparation of the corresponding 6-methyl-indazole compound (cf. the process stages described in Example 4(a)–(f).

e. by the reaction of 1-acetyl-4-(2,3-epoxypropoxy)-7-methyl-indazole with tert.-butylamine:
  1-[7-methyl-indazolyl-(4)-oxy]-3-tert.-butylamino-propan-2-ol; m.p. 118,5°–119,5° C.

f. by the reaction of 1-acetyl-4-(2,3-epoxypropoxy)-5-ethyl-indazole with isopropylamine:
  1-[6-ethyl-indazolyl-(4)-oxy]-3-isopropylamino-propan-2-ol; m.p. 77°–78° C.

The 1-acetyl-4-(2,3-epoxypropoxy)-6-ethyl-indazole used as starting material is prepared by several stages in a manner analogous to that used for the preparation of the corresponding 6-methyl-indazole compound (cf. the process stages described in Example 4(a)–(f);

g. by the reaction of 1-acetyl-4-(2,3-epoxypropoxy)-6-ethyl-indazole with tert.-butylamine:
  1-[6-ethyl-indazolyl-(4)-oxy]-3-tert.-butylamino-propan-2-ol.

EXAMPLE 6

1-[6-Methyl-indazolyl-(4)-oxy]-3-[1-methylthiopropyl-(2)-amino]-propan-2-ol 3.0 g. 4-(2,3-Epoxypropoxy)-6-methyl-indazole are stirred for 8 hours at 50°–60° C. in an atmosphere of nitrogen with 15 ml. methylthioisopropylamine. The reaction mixture is evaporated to dryness and about 40 ml. diethyl ether and a few drops of methanol are added to the residue. After trituration and complete crystallization, the product is filtered off with suction and then washed with diethyl ether. There are obtained 3.2 g. (70.4% of theory) 1-[6-methyl-indazolyl-(4)-oxy]-3-[1-methylthiopropyl-(2)-amino]-propan-2-ol; m.p. 91°–94° C.

From ethyl acetate, with the use of active charcoal and fullers' earth, there are obtained 1.7 g. of colorless crystals; m.p. 102°–104° C.

The 4-(2,3-epoxypropoxy)-6-methyl-indazole used as starting material is prepared as follows:

18 g. of the acetyl compound described in Example 4 are stirred for 8 hours in 200 ml. methylene chloride and 100 ml. liquid ammonia. The reaction mixture is then evaporated to dryness and the residue is treated with water. There are obtained 14.5 g. 4-(2,3-epoxypropoxy)-6-methyl-indazole in the form of colorless crystals; m.p. 123°–125° C. After recrystallization from methylene chloride (after cooling to −80° C.): m.p. 138°–139° C. but in the case of a slower heating rate, the substance melts at a lower temperature.

EXAMPLE 7

1-[6-Methyl-indazolyl-(4)-oxy]-3-(methylthio-tert.-butyl-amino)-propan-2-ol 3.0 g. 4-(2,3-Epoxypropoxy)-6-methyl-indazole are stirred for 12 hours under an atmosphere of nitrogen at 50°–60° C. with 15 ml. methylthio-tert.-butylamine. After evaporating the reaction mixture to dryness in a vacuum, the residue is triturated with diethyl ether. There are obtained 3.8 g. (80.0% of theory) 1-[6-methyl-indazolyl-(4)-oxy]-3-(methylthio-tert.-butylamino)-propan-2-ol; m.p. 110°–112° C.

Recrystallized from ethyl acetate, with the use of active charcoal and fullers' earth, there are obtained therefrom 2.8 g. of colorless crystals; m.p. 113°–115° C.

EXAMPLE 8

1-[6-Methyl-indazolyl-(4)-oxy]-3-isopropylaminopropan-2-ol 0.5 g. 4-(3-Chloro-2-hydroxy-propoxy)-6-methylindazole are heated in a glass autoclave for 9 days at 70° C. in 100 ml. isopropylamine. The reaction mixture is evaporated to dryness and the residue is taken up in water, rendered alkaline and extracted with chloroform. After drying over anhydrous sodium sulphate, the extract is evaporated and the residue (0.55 g) is recrystallized from ethyl acetate, with the use of fullers' earth. There are obtained crystals with a melting point of 154°–156° C. which show no melting point depression in admixture with the product obtained according to Example 4 from 1-acetyl-4-(2,3-epoxypropoxy)-6-methyl-indazole.

The 4-(3-chloro-2-hydroxypropoxy)-6-methyl-indazole used as starting material is prepared as follows:

A solution of 2.7 g. 4-(2,3-epoxypropoxy)-6-methylindazole in 10 ml. glacial acetic acid is introduced, while stirring, into 10 ml. of glacial acetic acid which have been saturated with hydrogen chloride at ambient temperature. After 1 hour at ambient temperature, the reaction mixture is poured into 300 ml. water and neutralized with sodium bicarbonate, a viscous oil thereby separating out which solidifies after stirring for a comparatively long time or upon triturating with toluene. When recrystallized from toluene, with the use of fullers' earth, the product is obtained in the form of colorless needles; m.p. 171°–172° C.

The following tests were carried out to determine the cardiac β-receptor blocking activity of certain test compounds by determining the inhibition of the heart beat frequency increase induced by intravenous administration of isoprenalin (=3,4-dihydroxy-α-[(isopropylamino)-methyl]benzylalcohol).

The test compounds representative of the invention were the following:

Compound I: 1-[Indazolyl-(4)-oxy]-3-isopropyl-aminopropan-2ol
Compound II: 1-[Indazolyl-(4)-oxy]-3-tert.-butylaminopropan-2-ol
Compound III: 1-[6-Methyl-indazolyl-(4)-oxy]-3-isopropylaminopropan-2-ol
Compound IV: 1-[6-methyl-indazolyl-(4)-oxy]-3-tert.-butylaminopropan-2-ol
Compound V: 1-[6-methyl-indazolyl-(4)-oxy]-3-[1-methylthiopropyl-(2)-amino]propan-2-ol
Compound VI: 1-[6-methyl-indazolyl-(4)-oxy]-3-(methylthio-tert.-butylamino)propan-2-ol.

As comparison compound there was included:

Compound A: 1-Isopropylamino-3-(1-naphthoxy)-2-propanol (Propranolol)

These compounds were tested in the following manner:

The β-receptor blocking activity of the test compounds was tested on wake rabbits weighing between 2 to 3.5 kg and kept in wooden cages. EKG-electrodes were inserted into the hind quarters of the rabbits s.c. (II. lead) and the heart frequency was measured using an integrator (15 seconds) as a digital value. The test compounds were then infused through a small tube to the ear vein of the rabbits over a period of 15 minutes. 30 Minutes after the infusion isoprenalin was injected intravenously at 1 μg/kg.

The results are set forth in terms of inhibition of isoprenalin tachycardia, and are set forth in the table below.

TABLE

| Test Substance | Blocking of Isoprenalin Tachycardia in Wake Rabbits | | DE 250* μg/kg i.v. |
|---|---|---|---|
| | Dosage mg/kg i.v. | Heartbeat Frequency (min.) $\bar{x} \pm s_{\bar{x}}$ | |
| Control | without Iso-prenalin | 209 ± 9 | — |
| Control | with Iso-prenalin | 338 ± 10 | — |
| Compound A (Propranolol) | 0.01 | 342 ± 5 | 400 |
| | 0.1 | 309 ± 9 | |
| | 0.25 | 259 ± 7 | |
| | 0.5 | 248 ± 6 | |
| | 1.0 | 210 ± 8 | |
| | 4.0 | 191 ± 6 | |
| Compound I (Example 1) | 0.001 | 314 ± 8 | 30 |
| | 0.005 | 280 ± 6 | |
| | 0.01 | 259 ± 7 | |
| | 0.1 | 237 ± 6 | |
| | 0.5 | 239 ± 4 | |
| | 1.0 | 237 ± 2 | |
| | 5.0 | 238 ± 8 | |
| Compound II (Example 2) | 0.001 | 294 ± 7 | |
| | 0.005 | 264 ± 9 | 20 |
| | 0.01 | 253 ± 4 | |
| | 0.1 | 237 ± 10 | |
| | 0.5 | 242 ± 4 | |
| | 1.0 | 238 ± 6 | |
| Compound III (Example 4) | 0.001 | 299 ± 6 | |
| | 0.01 | 236 ± 7 | 6 |
| | 0.1 | 214 ± 6 | |
| | 3.0 | 199 ± 11 | |
| Compound IV (Example 5) | 0.0003 | 327 ± 7 | |
| | 0.003 | 258 ± 15 | 4 |
| | 0.007 | 235 ± 7 | |
| | 0.03 | 198 ± 9 | |
| Compound V (Example 6) | 0.01 | 315 ± 11 | |
| | 0.03 | 258 ± 10 | 40 |
| | 1.0 | 228 ± 11 | |
| Compound VI (Example 7) | 0.01 | 276 ± 10 | |
| | 0.03 | 229 ± 6 | 18 |
| | 0.1 | 222 ± 8 | |

*Interpolated dosage which limits the frequency increas to 250 beats/min.

The above data show that the inventive compounds are already effective at a dosage much smaller than those required of the comparison substances.

The compounds according to the present invention are thus unexpectedly superior in effectiveness to known compounds and thus present a valuable contribution to the art.

The dosages of the novel compounds of the present invention depend on the age, weight, and condition of the patient being treated. Generally speaking, for adultoral administration, the preferred unit dosage of active compound with suitable pharmaceutical diluent or lubricant is 1 mg.–40 mg. four times a day. In general the oral dosage is 20–40 mg., whereas the intravenous dosage is generally 1–5 mg., four times a day.

For preparing therapeutic compositions such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administrations.

It will be appreciated that the instant specification and examples are set forth by way of illustration and not limitation, and that various modifications and changes may be made without departing from the spirit and scope of the present invention.

What is claimed is:

1. Indazolyl-(4)-oxy-propanolamine compound of the formula:

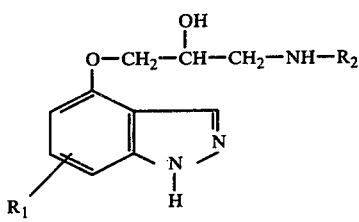

wherein
R₁ is hydrogen or lower alkyl and
R₂ is straight-chain or branched one lower alkyl which is optionally substituted by lower alkylthio;
and the pharmacologically compatible salts thereof.

2. Indazolyl-(4)-oxy-propanolamine compound as claimed in claim 1 wherein R₁ is hydrogen.

3. Indazolyl-(4)-oxy-propanolamine compound as claimed in claim 1 wherein R₁ is lower alkyl of up to 4 carbon atoms.

4. Indazolyl-(4)-oxy-propanolamine compound as claimed in claim 1 wherein R₂ is lower alkyl of up to 5 carbon atoms.

5. Indazolyl-(4)-oxy-propanolamine compound as claimed in claim 1 wherein R₂ is isopropyl or tert.-butyl.

6. Indazolyl-(4)-oxy-propanolamine compound as claimed in claim 1 wherein R₂ is alkylthioalkyl with up to 3 carbon atoms in the alkylthio moiety and up to 5 carbon atoms in the alkyl moiety.

7. Indazolyl-(4)-oxy-propanolamine compound as claimed in claim 1, namely 1-[indazolyl-(4)-oxy]-3-tert.-butylaminopropan-2-ol.

8. Indazolyl-(4)-oxy-propanolamine compound as claimed in claim 1, namely 1-[6-methyl-indazolyl-(4)-oxy]-3-isopropylaminopropan-2-ol.

9. Indazolyl-(4)-oxy-propanolamine compound as claimed in claim 1, namely 1-[6-methyl-indazolyl-(4)-oxy]-3-tert.-butylaminopropan-2-ol.

10. Indazolyl-(4)-oxy-propanolamine compound as claimed in claim 1, namely 1-[6-methyl-indazolyl-(4)-oxy]-3-(methylthio-tert.-butylamino)-propan-2-ol.

11. Therapeutic composition for the treatment or prevention of a recurrence of cardiac and circulatory diseases comprising a pharmaceutically acceptable carrier and in therapeutically effective amounts an indazolyl-(4)-oxypropanolamine compound as claimed in claim 1.

12. Method of combatting or preventing a recurrence of cardiac and circulatory infirmities which method comprises administering to a subject an effective adrenergic β-receptor blocking amount of an indazolyl-(4)-oxypropanolamine compound of the formula

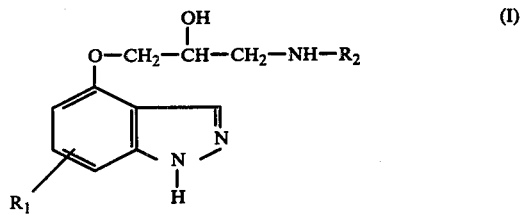

wherein
R₁ is hydrogen or lower alkyl; and
R₂ is straight-chain or branched lower alkyl which can be substituted by one lower alkylthio;
and the pharmacologically compatible salts thereof.

13. Method as claimed in claim 12 wherein said compound is
1-[indazolyl-(4)-oxy]-3-tert.-butylaminopropan-2-ol;
1-[6-methyl-indazolyl-(4)-oxy]-3-isopropylaminopropan-2-ol;
1-[6-methyl-indazolyl-(4)-oxy]-3-tert.-butylaminopropan-2-ol; or
1-[6-methyl-indazolyl-(4)-oxy]-3-(methylthio-tert.-butylamino)-propan-2-ol.

14. Method as claimed in claim 12 wherein said compound is administered at a dosage of 1 to 40 mg up to four times a day.

15. Method as claimed in claim 12 wherein said compound is applied orally in dosages of 20 to 40 mg.

16. Method as claimed in claim 12 wherein said compound is administered intravenously at a dosage of from 1 to 5 mg per dosage.